United States Patent [19]

Inoue et al.

[11] Patent Number: 4,873,391

[45] Date of Patent: Oct. 10, 1989

[54] PROCESS FOR PRODUCING ISOBUTYLENE

[75] Inventors: Kazutaka Inoue; Toshihiro Sato; Masao Kobayashi, all of Hiroshima, Japan

[73] Assignee: Mitsubishi Rayon Company, Ltd., Tokyo, Japan

[21] Appl. No.: 235,694

[22] Filed: Aug. 17, 1988

Related U.S. Application Data

[63] Continuation of Ser. No. 80,008, Jul. 31, 1987, abandoned.

[30] Foreign Application Priority Data

Aug. 6, 1986 [JP] Japan ................................. 61-184961

[51] Int. Cl.$^4$ ............................................... C07C 1/24
[52] U.S. Cl. ..................................... 585/639; 585/640
[58] Field of Search ................................ 585/639, 640

[56] References Cited

U.S. PATENT DOCUMENTS

| | | | |
|---|---|---|---|
| 2,377,026 | 5/1945 | Miller | 585/639 |
| 3,665,048 | 5/1972 | Grane et al. | 585/639 |
| 4,012,456 | 3/1977 | Chaplits | 585/639 |
| 4,036,905 | 7/1977 | Kornfeld | 585/639 |
| 4,234,752 | 11/1980 | Wu | 585/639 |
| 4,331,824 | 5/1982 | Ikeda et al. | 585/639 |
| 4,343,959 | 8/1982 | Kida et al. | 585/639 |
| 4,423,271 | 12/1983 | Oberans et al. | 585/639 |
| 4,529,827 | 7/1985 | Drake | 585/639 |

FOREIGN PATENT DOCUMENTS

| | | | |
|---|---|---|---|
| 523702 | 4/1956 | Canada | 585/639 |
| 0082937 | 7/1983 | European Pat. Off. | |
| 7213250 | 10/1967 | Japan | 585/639 |
| 54-135710 | 10/1979 | Japan | |
| 54-138506 | 10/1979 | Japan | |
| 1000026 | 1/1986 | Japan | 585/639 |

Primary Examiner—Asok Pal
Attorney, Agent, or Firm—Cushman, Darby & Cushman

[57] ABSTRACT

A process for production of isobutylene by dehydration reaction of t-butyl alcohol or its aqueous solution is provided wherein the dehydration reaction is carried out in gaseous phase on fixed-bed type silica-alumina catalyst with adding non-reactive gas and/or water vapor to feed gas or reaction gas and/or with diluting at least a part of the catalyst with a carrier.

10 Claims, No Drawings

PROCESS FOR PRODUCING ISOBUTYLENE

This is a continuation of application Ser. No. 080,008, filed July 31, 1987, which was abandoned upon the filing hereof.

BACKGROUND OF THE INVENTION

This invention relates to a process for producing isobutylene by dehydration reaction of t-butyl alcohol.

Isobutylene is used as a starting material for polymers such as butyl rubber, polybutene, etc. It is also used as starting material for industrial products such as isoprene, BHT, t-butylcatechol, t-butyl esters of various carboxylic acids, etc. Recently, it is noticed as source of starting materials for production of methyl methacrylate.

It has been well known that isobutylene is produced by dehydration of t-butyl alcohol in the presence of an acid catalyst.

The dehydration reaction in liquid phase is usually carried out in a homogeneous system using a strong acid such as sulfuric acid. However, this method requires expensive anticorrosion equipment and furthermore produces waste acids and is industrially not preferred due to these problems.

Recently, for solving these problems, it has been proposed to effect the above dehydration reaction in heterogeneous systems using strongly acidic ion exchange resins containing sulfonic acid group as a catalyst (U.S. Pat. No. 4,012,456, EP 82,937 and Japanese Patent Kokai Nos. 135710/79 and 138506/79). However, proportion of water increases under high conversions, resulting in reduction of reaction velocity and polymerization of isobutylene, a side-reaction, proceeds to cause decrease of yields, since t-butyl alcohol is in equilibrium with isobutylene and water in reaction of liquid phase system. Thus, in order to obtain high yields, it is necessary to control the conversion rate and unaltered materials are recovered and recycled to the reaction system. This complicates the production process.

It is also well known that isobutylene is easily produced by bringing t-butyl alcohol into contact in gas phase with solid acids such as solid phosphoric acid, active alumina, silica-alumina, etc. at high temperatures. U.S. Pat. No. 4,036,905 discloses industrial production of isobutylene using this reaction where the reaction is effected at a high temperature of 246°–413° C. on a solid acid catalyst. In order to effect the dehydration reaction with high yields, it is necessary to restrain the side-reaction of polymerization of isobutylene and thus it is preferred to effect the reaction at higher temperatures. However, it is difficult to economically and inexpensively obtain heat sources for high temperatures and besides extra energy is required to heat the reaction gas to high temperatures and cool to temperatures for easy handling after completion of the reaction. Under the circumstances, there has been demanded a method according to which high yields is attained by carrying out the reaction economically and at lower temperatures.

However, there is no method to produce isobutylene from t-butyl alcohol or its aqueous solution in high yields at lower temperatures with highly active catalysts.

According to the process disclosed in Japanese Patent Kokai No. 13250/72, the dehydration reaction is effected at relatively lower temperatures of 50°–300° C. to attain high yields, but this patent publication is silent on selectivity of the dehyeration reaction. After the reaction was repeated with various catalysts using 90% aqueous t-butyl alcohol solution, it is found that selectivity of isobutylene is lower as activity of catalysts employed is higher and reaction temperature is lower and that the reaction is desirably carried out at higher reaction temperatures, preferably higher than 300° C. in order to obtain high yields.

The inventors have made researches on various catalysts for economical production of isobutylene from t-butyl alcohol or inexpensively available aqueous solutions thereof as a starting material by gaseous phase dehydration reaction. As a result, it has been found that silica-alumina has high activity at low temperatures. However, with reference to the yield, it has been found that conversion rate and selectivity of reaction greatly vary depending on space velocity of reaction gas and reaction temperature and higher yields are difficult to obtain with decrease in reaction temperature.

Main factor for the reduction of selectivity under high conversion rate of reaction is polymerization reaction of isobutylene produced. The polymerization reaction of isobutylene can be restrained to some extent when reaction is carried out at higher temperatures, but it gradually proceeds at lower reaction temperatures to cause reduction of selectivity of isobutylene. If a process where the polymerization reaction of isobutylene can be restrained in spite of low temperature reaction. isobutylene can naturally be produced in high yields and furthermore, after-treatment of the produced gas can be easily accomplished by known method. Thus, this process will be very attractive as a process for industrial production of isobutylene.

The inventors have made researches separately on dehydration reaction of t-butyl alcohol in gaseous phase with use on silica-alumina catalyst and polymerization reaction of isobutylene.

The dehydration reaction of t-butyl alcohol proceeded very easily on silica-alumina catalyst and conversion rate enough for practical use was obtained at about 150° C. However, with increase in conversion rate, selectivity of isobutylene abruptly decreased to cause conspicuous production of diisobutylene and furthermore triisobutylene. On the other hand, it was experimentally confirmed that polymerization reaction of isobutylene very easily takes place at about 150° C. and at the higher temperatures it becomes difficult to occur.

As a result of the inventors' extensive researches on the conditions where polymerization of isobutylene is difficult to occur even at relatively low temperatures, it has been found that isobutylene can be obtained at high selectivity even under high conversion rate of reaction by incorporating a non-reactive gas and/or water vapor into feed gas or reaction gas or by diluting at least a part of silica-alumina catalyst with a carrier or by combination of these means.

SUMMARY OF THE INVENTION

That is, this invention relates to a process for production of isobutylene by gaseous phase dehydration reaction of t-butyl alcohol or an aqueous solution thereof as a starting material on a fixed-bed silica-alumina catalyst at 100°–450° C. wherein non-reactive gas and/or water vapor are incorporated into feed gas or the gas is passed on the catalyst at least a part of which is diluted or replaced with a carrier.

DESCRIPTION OF THE INVENTION

The non-reactive gas incorporated into feed gas or reaction gas in the process of this invention must be a substance which does not cause side reactions. Substances known as inert gases can be naturally used and especially, nitrogen, air diluted with nitrogen to low oxygen concentration, gases prepared from combustion exhaust gases, etc. may be practically used, but any substances may be used as far as they cause no side reactions and give no damages to others in handling.

In the process of this invention, water vapor has the similar effects to those of non-reactive gas and may also be used. Water vapor is a product of the dehydration reaction of this invention, but when reaction is effected with additional incorporation of fresh water vapor, selectivity of isobutylene can be markedly increased. Especially, water vapor can be easily removed from reaction product gas and is useful.

In the process of this invention, silica-alumina catalyst is used is a fixed-type reactor and carriers used for dilution of the packed catalyst include substances which are less active to the dehydration reaction of t-butyl alcohol and the polymerization reaction of isobutylene than silica-alumina catalyst or show no activity to the reaction. Examples are silica, alumina, silicon carbide, activated carbon, zeolite, etc. This invention is not limited thereto.

As the silica-alumina catalysts used in this invention, those which are commercially available may be used as they are. There may also be used those which are inactivated partially on acid active points by heat treatment at high temperatures, treatment with steam or treatment with aqueous alkali solution for obtaining catalysts of proper activity. Generally, they contain 10-30 wt % of $Al_2O_3$ and have properties of a specific surface area of 100-1000 $m^2/g$ and a total pore volume of 0.3-1.0 cc/g.

In dehydration reaction of t-butyl alcohol, a selectivity of nearly 100% can be obtained until a certain degree of conversion rate. Therefore, the higher reaction efficiency can be obtained when the dilution of feed gas or reaction gas with non-reactive gas and/or water vapor or dilution of catalyst with a carrier according to this invention is effected at the point where selectivity to isobutylene begins to decrease. This is preferred.

That is, upon analyzing the reactivity when flow type reaction is carried out at a predetermined temperature under the conditions of no dilution of feed gas and no dilution of silica-alumina catalyst, dilution of reaction gas with non-reactive gas and/or water vapor is effected at an appropriate position of reactor or the catalyst layer thereafter is diluted with a suitable carrier. Combination thereof is especially preferred. However, if the initial reaction velocity can be somewhat sacrificed, the high yields can also be obtained even when the feed gas is diluted from the first or the whole of the packed catalyst is diluted with a suitable carrier. Furthermore, dilution of feed gas or reaction gas and dilution of the catalyst layer may be carried out stepwise. Dilution of feed gas with non-reactive gas and/or water vapor is effected within the range of 0.01-100, preferably 0.1-10 times in volume as much as feed gas. Dilution of catalyst layer with a carrier is effected within the range of 0.01-100, preferably 0.1-10 times in volume as much as the silica-alumina catalyst packed.

Since in the dehydration reaction of t-butyl alcohol, water is produced and further, water vapor effectively acts of the selectivity of reaction, there are no adverse effects on the reaction even if t-butyl alcohol used as a starting material is an aqueous solution and generally inexpensively available aqueous t-butyl alcohol solution of a wide variety of concentrations may be used in this invention.

The process of this invention exhibits remarkable effects at relatively low temperatures, but further higher selectivity can be obtained by the present process also in high temperature area where high selectivity is generally obtained. The temperature range of 100°-450° C. is preferred.

The process of this invention can be worked under any pressures as far as the reaction system is operated in gaseous phase. However, with increase in pressure, activity and selectivity of the reaction decrease. Preferred pressure range is 0.01 atm-10 atm.

The reaction gas obtained with high selectivity can be subjected to known treatments, for example, removal of condensing components by condenser, distillation, if necessary, whereby industrially useful isobutylene can be obtained.

The following nonlimiting examples further illustrate this invention.

COMPARATIVE EXAMPLES 1-5

330 cc of commercially available molded Silica-alumina catalyst N631L (5 mm$\phi$×5 mm) (manufactured by Nikki Chemical Co.) without dilution was packed in a stainless steel reaction tube of 25 mm inner diameter and 700 mm length to form a catalyst layer. Through this catalyst layer was passed a feed gas prepared by total evaporation of 90% aqueous t-butyl alcohol solution and further preheating it at a space velocity of 400 l/h and continuous reaction was effected at 160° C. After the reaction became steady, reaction was carried out changing only the space velocity. The results are shown in Table 1.

TABLE 1

| Experiment No. | 1 | 2 | 3 | 4 | 5 |
| --- | --- | --- | --- | --- | --- |
| Flow rate of feed gas (l/h) | 132 | 115.5 | 99 | 82.5 | 66 |
| Space velocity (1/h) | 400 | 350 | 300 | 250 | 200 |
| Conversion rate of t-butyl alcohol (%) | 91.2 | 93.5 | 95.6 | 98.1 | 99.3 |
| Selectivity of isobutylene (%) | 97.1 | 96.3 | 95.1 | 92.9 | 89.9 |
| Yield of isobutylene (%) | 88.6 | 90.1 | 90.9 | 91.1 | 89.3 |

EXAMPLES 1-5

Reactions were effected in the same manner as in Comparative Example 1 except that nitrogen gas or water vapor preheated to 160° C. was supplied at the intermediate portion of the reaction tube, namely, at a position of 350 mm from the inlet of the tube with changing the flow rate. The results are shown in Table 2 as Examples 1-4. Results obtained when water vapor was supplied at the inlet of the reaction tube are also shown in Table 2 as Example 5.

TABLE 2

| Example No. | 1 | 2 | 3 | 4 | 5 |
| --- | --- | --- | --- | --- | --- |
| Reaction temperature (°C.) | 160 | 160 | 160 | 160 | 160 |
| Flow rate of feed gas (l/h) | 33 | 22 | 33 | 11 | 33 |
| Kind of dilution gas | $N_2$ | $N_2$ | $H_2O$ | $H_2O$ | $H_2O$ |
| Flow rate of dilution | 33 | 44 | 33 | 55 | 33 |

TABLE 2-continued

| Example No. | 1 | 2 | 3 | 4 | 5 |
|---|---|---|---|---|---|
| gas (l/h) | | | | | |
| Conversion rate of t-butyl alcohol (%) | 99.7 | 99.2 | 99.3 | 99.0 | 98.5 |
| Selectivity of isobutylene (%) | 94.6 | 95.8 | 94.8 | 97.1 | 96.1 |
| Yield of isobutylene (%) | 94.3 | 95.0 | 94.1 | 96.1 | 94.7 |

EXAMPLES 6–12

The whole of the catalyst evaluated in Examples 1–5 was taken out from the reaction tube and the whole or a part of the catalyst layer was diluted with an alumina ceramics carrier or an activated alumina of the similar particle size. Thus diluted catalyst of 330 cc in total volume was packed again in the reaction tube. In the same manner as in Examples 1–5, t-butyl alcohol evaporated and preheated was fed to the reaction tube and water vapor was supplied at the intermediate portion of the reaction tube to carry out reaction. The results are shown in Table 3.

TABLE 3

| Example No. | 6 | 7 | 8 | 9 | 10 | 11 | 12 |
|---|---|---|---|---|---|---|---|
| Carrier for dilution of catalyst layer | A | A | A | B | B | B | A |
| Diluted part of catalyst layer | The whole area | Latter half | Latter half | The whole area | Latter two-thirds | Latter half | The whole area |
| Dilution ratio | 2 times | 2 times | 4 times | 2 times | 3 times | 4 times | 4 times |
| Flow rate of feed gas (l/h) | 11.5 | 34 | 28 | 11.5 | 25 | 28 | 14 |
| Flow rate of water vapor for dilution (l/h) | 21.5 | 68 | 84 | 21.5 | 50 | 84 | 0 |
| Reaction temperature (°C.) | 160 | 185 | 210 | 160 | 190 | 200 | 160 |
| Conversion rate of t-butyl alcohol (%) | 99.7 | 99.1 | 99.4 | 99.8 | 99.5 | 99.7 | 99.2 |
| Selectivity of isobutylene (%) | 98.4 | 98.6 | 99.0 | 98.0 | 97.8 | 98.4 | 94.3 |
| Yield of isobutylene (%) | 98.1 | 97.7 | 98.4 | 97.8 | 97.3 | 98.1 | 93.5 |

A: Alumina ceramics carrier
B: Activated alumina

COMPARATIVE EXAMPLE 6

330 cc of N631L was packed in the same reaction tube as in Comparative Example 1, to which was fed t-butyl alcohol evaporated and preheated to 160° C. at a flow rate of 45 l/h under normal state to carry out reaction at 160° C. Selectivity of isobutylene was 84.8% at a conversion rate of t-butyl alcohol of 99.5%.

COMPARATIVE EXAMPLE 7

10 cc of molded silica-alumina catalyst N631HN (manufactured by Nikki Chemical Co.) crushed to 10–20 meshes was packed in the central portion of a glass reaction tube of 12 mm inner diameter and 300 mm length and silicon carbide was packed before and behind the packed silica-alumina catalyst. This reaction tube was placed in an air bath of 400° C. and t-butyl alcohol vapor was passed at 400° C. therethrough at a flow rate of 10 l/h under normal state. Selectivity of isobutylene was 98.4% at a conversion rate of t-butyl alcohol of 100%. That is, when the reaction was effected at high temperature, selectivity of isobutylene increased, but according to the process of this invention, further superior results were obtained as shown in the following Example 13.

EXAMPLE 13

A catalyst layer comprising a thorough mixture of 5 cc of the same catalyst (10–20 meshes) as in Comparative Example 7 and 5 cc of silicon carbide of the same particle size was provided in the same manner as in Comparative Example 7 and a mixed gas of t-butyl alcohol and water vapor (1:1) was passed therethrough at 400° C. at a flow rate of 3 l/h under normal state. Selectivity of isobutylene was 99.6% at a conversion rate of t-butyl alcohol of 100%.

We claim:

1. A process for producing isobutylene by dehydration of a feed gas of t-butyl alcohol of at least 90% of purity or its aqueous solution in gaseous phase on a fixed-bed type silica-alumina catalyst at a temperature in the range of 100°–210° C., wherein water vapor is added to feed gas and at an intermediate portion of said fixed bed catalyst and at least the last half of the catalyst located near the outlet end of the fixed-bed of catalyst is diluted with a carrier which has lower activity than the used catalyst.

2. A process according to claim 1 wherein the addition of water vapor to feed gas and the dilution of the catalyst with a carrier is made at the same time when selectivity to isobutylene begins to decrease.

3. A process according to claim 1 wherein dilution of the feed gas with water vapor is made within the range of 0.01–100 times in volume as much as the feed gas.

4. A process according to claim 3 wherein the range is 0.01–10 times.

5. A process according to claim 1 wherein dilution of a catalyst with a carrier is made within the range of 0.01–100 times in volume as much as the catalyst packed and at least the half of the catalyst is diluted with a carrier.

6. A process according to claim 5 wherein the range is 0.1–10 times.

7. A process according to claim 1 wherein the water vapor is steam.

8. A process according to claim 1 wherein the feed gas consists essentially of t-butyl alcohol.

9. A process according to claim 1 wherein the carrier is a substance which is lower than silica-alumina catalyst in activity to dehydration reaction of t-butyl alcohol and polymerization reaction of isobutylene than silica-alumina catalyst or has no activity to the reactions.

10. A process according to claim 1 wherein the silica-alumina catalyst contains 10–30 wt % of $Al_2O_3$ and has a specific surface area of 100–1000 m$^2$/g and a total pore volume of 0.3–1.0 cc/g.

* * * * *